(12) United States Patent
Lu et al.

(10) Patent No.: US 11,404,206 B2
(45) Date of Patent: Aug. 2, 2022

(54) MONITORING SYSTEM

(71) Applicant: Verso Biosense Group Limited, Abingdon (GB)

(72) Inventors: Shilong Lu, Southampton (GB); Tianze Guo, Southampton (GB)

(73) Assignee: Verso Biosense Group Limited, Abingdon (GB)

( * ) Notice: Subject to any disclaimer, the term of this patent is extended or adjusted under 35 U.S.C. 154(b) by 0 days.

(21) Appl. No.: 16/957,356

(22) PCT Filed: Dec. 24, 2018

(86) PCT No.: PCT/GB2018/053772
§ 371 (c)(1),
(2) Date: Jun. 23, 2020

(87) PCT Pub. No.: WO2019/122937
PCT Pub. Date: Jun. 27, 2019

(65) Prior Publication Data
US 2020/0335274 A1 Oct. 22, 2020

(30) Foreign Application Priority Data
Dec. 24, 2017 (GB) ...................................... 1721863

(51) Int. Cl.
*H01F 38/14* (2006.01)
*A61B 5/03* (2006.01)
(Continued)

(52) U.S. Cl.
CPC ............. *H01F 38/14* (2013.01); *A61B 5/035* (2013.01); *A61B 5/4325* (2013.01); *H04B 5/0031* (2013.01)

(58) Field of Classification Search
CPC ....... H01F 38/14; A61B 5/035; A61B 5/4325; A61B 5/6875; A61B 5/0031; H04B 5/0031; H04B 5/0037; H02J 7/00034; H02J 50/10
See application file for complete search history.

(56) References Cited

U.S. PATENT DOCUMENTS 9,653,948 B2 * 5/2017 Polu ........................ H03F 3/195
2004/0236193 A1 * 11/2004 Sharf .................. A61B 5/6882
600/302
(Continued)

FOREIGN PATENT DOCUMENTS

WO 2016081013 A1 5/2016

OTHER PUBLICATIONS

Basar, "Stable and High-Efficiency Wireless Power Transfer System for Robotic Capsule Using a Modified Helmholtz Coil" IEEE Transactions on Industrial Electronics, vol. 64, No. 2, Feb. 2017 (Year: 2017).*
(Continued)

*Primary Examiner* — Pinping Sun
(74) *Attorney, Agent, or Firm* — Armstrong Teasdale LLP (57) ABSTRACT

A monitoring system is described which comprises a sensor device for generating sensor data, the sensor device having a secondary coil, and a receiver device having a controller, and a primary coil for wirelessly communicating with the sensor device, the receiver device being operable to wirelessly charge the sensor device via inductive coupling between the primary and secondary coils. A quality factor of the primary coil is controllable, and the controller is operable to control the quality factor of the primary coil to be higher when the receiver device is wirelessly charging the sensor device than when the receiver device is receiving sensor data from the sensor device. As a result, the same coil can be used both for efficient power transfer (wireless
(Continued)

charging) by using the coil in a (relatively) high quality factor mode, and for reliable data communications by using the coil in a (relatively) low quality factor mode.

15 Claims, 7 Drawing Sheets

(51) Int. Cl.
*A61B 5/00* (2006.01)
*H04B 5/00* (2006.01)

(56) References Cited

U.S. PATENT DOCUMENTS

| | | | |
|---|---|---|---|
| 2009/0230777 A1* | 9/2009 | Baarman | H01F 38/14 307/104 |
| 2011/0241437 A1* | 10/2011 | Kanno | H01F 38/14 307/104 |
| 2012/0056485 A1 | 3/2012 | Haruyama | |
| 2012/0274270 A1* | 11/2012 | Dinsmoor | H02J 50/10 320/108 |
| 2013/0069445 A1* | 3/2013 | Waffenschmidt | H01F 27/2804 307/104 |
| 2013/0107928 A1* | 5/2013 | Cox | H04L 1/0006 375/224 |
| 2013/0207744 A1* | 8/2013 | Singh | H04B 5/0075 333/175 |
| 2013/0281016 A1* | 10/2013 | McFarthing | H04B 5/00 455/41.1 |
| 2014/0191710 A1* | 7/2014 | van Lammeren | H04B 5/0037 320/108 |
| 2014/0197783 A1 | 7/2014 | Kim et al. | |
| 2014/0323043 A1* | 10/2014 | Shana'a | H04B 5/0031 455/41.1 |
| 2015/0209591 A1* | 7/2015 | Meskens | A61N 1/37223 607/60 |
| 2015/0214752 A1* | 7/2015 | Gluzman | H02J 50/40 307/104 |
| 2016/0022216 A1* | 1/2016 | Goldshtein | H02J 50/70 600/486 |
| 2016/0133387 A1 | 5/2016 | Kanno | |
| 2016/0294225 A1* | 10/2016 | Blum | H02J 5/005 |
| 2017/0288734 A1 | 10/2017 | Zhou et al. | |
| 2017/0288736 A1* | 10/2017 | Zhou | H01Q 1/2225 |
| 2017/0340476 A1* | 11/2017 | Kuster | A61B 5/002 |
| 2018/0367187 A1* | 12/2018 | McFarthing | H04B 5/0031 |
| 2020/0060607 A1* | 2/2020 | Morgan | A61B 5/0002 |

OTHER PUBLICATIONS

Definitions,"The definition of inductive coupling," pp. 1-3 (Year: NA).*

International Search Report, International Application No. PCT/GB2018/053772, dated Jun. 25, 2019, 3 pages.

Written Opinion, International Application No. PCT/GB2018/053772, 7 pages.

GB Intellectual Property Office, Search Report, Application No. GB1721863.7, 4 pages.

* cited by examiner

| Common RFID | | | | | | | |
|---|---|---|---|---|---|---|---|
| Power Transfer | | | | | | | |
| Downlink | | | | | | | |
| Uplink | | | | | | | |
| Fixed Coil | Low Q | | Low Q | | Low Q | Low Q | Low Q |

| Modified SEQ | | | | | | | | |
|---|---|---|---|---|---|---|---|---|
| Power Transfer | | | | | | | | |
| Diagnose | | | | | | | | |
| Downlink | | | | | | | | |
| Uplink | | | | | | | | |
| Adaptive Coil | High Q | Vary Q | Low Q | Low Q | High Q | | Low Q | Low Q |

MONITORING SYSTEM

CROSS-REFERENCE TO RELATED APPLICATIONS

This application is the 35 U.S.C. § 371 national phase of International Patent Application No. PCT/GB2018/053772, filed Dec. 24, 2018, which claims priority to Great Britain Patent Application No. 1721863.7, filed Dec. 24, 2017, both of which are incorporated herein by reference in their entirety.

TECHNICAL FIELD

The present invention relates to a monitoring system comprising a sensor device and a receiver device for both wirelessly charging the sensor device and wirelessly receiving sensor data from the sensor device. Embodiments of the invention relate to a body cavity monitoring system and method, and more specifically to an intra-uterine monitoring system and method. Embodiments of the present invention relate to a system for long-term, real-time, in-vivo measurement of biophysical parameters in a human uterus.

BACKGROUND

More than 30% of all human conceptions do not advance beyond 20 weeks of gestation. One in six couples suffer from infertility, and in around 25% of couples no clear reason is identified. Even after assistance from artificial reproductive technologies, take home baby rates have altered little in the last five to ten years. This may reflect the lack of understanding of the pathophysiological mechanisms and clinically relevant diagnostic approaches for interrogating uterine functions. An interaction between the intra-uterine environment (biophysical parameters, such as temperature, dissolved oxygen concentration and pH) and reproductive health is likely, but very little is known about the biophysical characteristics of the uterus and how they alter through the menstrual cycle. The available data is mostly derived from snapshot technology and wired sensor probes, both of which do not enable real-time long-term in-vivo monitoring.

In a previous patent application by the present Applicant, an intra-uterine monitoring system is described which addresses some of the limitations of the prior art. This monitoring system comprised a wearable receiver device and an implantable sensor device. Both the receiver device and the sensor device are provided with a respective coil antenna, permitting sensor data to be transmitted from the sensor device within the uterus to the receiver device which is external to the body. It is highly desirable for the implantable sensor device to be batteryless, both to enable the device to be as small as possible, and due to the problems associated with placing a chemical battery into the human body. Instead, the receiver device is able to wirelessly charge the sensor device using the inductive coupling between the coil antenna of the receiver device and the coil antenna of the sensor device.

It will be appreciated that the antenna of the sensor device, and the control circuitry associated with it, should be kept small, and operate at low power. In other words, the design constraints on the sensor device are very strict. There are various technical challenges associated with using the same antennae (on the receiver device and the sensor device) both to communicate data and transfer power.

The present invention is intended to address certain of these limitations.

SUMMARY OF THE INVENTION

According to an aspect of the present invention, there is provided a monitoring system, comprising:
a sensor device for generating sensor data, the sensor device having a secondary coil; and
a receiver device having a controller, and a primary coil for wirelessly communicating with the sensor device, the receiver device being operable to wirelessly charge the sensor device via inductive coupling between the primary and secondary coils;
wherein a quality factor of the primary coil is controllable; and
wherein the controller is operable to control the quality factor of the primary coil to be higher when the receiver device is wirelessly charging the sensor device than when the receiver device is receiving sensor data from the sensor device.

As a result of the quality factor being controllable, the same coil can be used both for efficient power transfer (wireless charging) by using the coil in a (relatively) high quality factor mode, and for reliable data communications by using the coil in a (relatively) low quality factor mode.

The quality factor may be controllable by modifying an electrical resistance associated with the primary coil. For example, a damping resistor could be switched in and out of series with the primary coil.

The quality factor of the primary coil may be selectable between a plurality of different levels. In a simple case, this could be two levels—a high level for wireless charging and a low level for receiving and/or transmitting data. In a more complicated case, this could be three levels, with an intermediate quality factor being used, for example if a different quality factor would be optimal for transmitting data compared with receiving data. For example, different data rates may be used for transmitting and receiving. If a faster data rate is used for receiving, then receiving will require a higher bandwidth and thus a lower quality factor. All other factors being equal, a coil with relatively high quality factor will output a higher field strength than a relatively low quality factor coil for the same input power. This will make the wireless charging more efficient. A coil with a relatively high quality factor corresponds to a lower resistance in the coil circuit, which will result in less heat generated than a low quality factor coil at the same input power. This has benefits for heat and thermal distribution within the receiver device.

Another reason for providing multiple different quality factors is to provide robustness to the communication link when the user is close to a metallic environment. For example, if the user is sitting in a car or sitting in a metal chair, then if the system is operating at a high quality factor, the presence of metal may detune the system, causing one or both of power transfer and communication to fail. However, a system with a lower quality factor will waste more power, which is generally undesirable, and may be unacceptable for a battery-powered wearable device, where power consumption needs to be relatively low. In order to alleviate this problem, the system may be configured to adaptively change the quality factor to accommodate the external environment while maintaining a reasonable battery life.

The receiver device may comprise a coil circuit, the coil circuit comprising the primary coil and a damping resistor, the damping resistor being switched into series with the primary coil to reduce the quality factor of the primary coil.

The coil circuit may comprise one or more further damping resistors, different ones or combinations of the damping resistors being used to control an amount of reduction of the quality factor.

The primary coil may be selectively configurable between a first mode in which it operates with a relatively high quality factor and a second mode in which it operates with a relatively low quality factor. In this case, the controller may be operable to select the second mode during a data transfer phase for receiving data from the sensor device and to select the first mode during a charging phase for charging the sensor device. The controller may be operable during a further data transfer phase for wirelessly transmitting a signal to the sensor device, to select the second mode. In this case, both outgoing communications (receiver device to sensor device) and incoming communications (sensor device to receiver device) are carried out in the same (second) mode, and thus with the same quality factor. As mentioned above, in some cases wireless transmission may benefit from a further (third) mode associated with a different quality factor. The quality factor of the third mode may be between the quality factors of the first and second modes. In this case, the controller may be operable during the further data transfer phase to select the third mode. Where the receiver device comprises a coil circuit, the coil circuit may comprise the primary coil and a damping resistor, the damping resistor being switched into series with the primary coil to reduce the quality factor to configure the primary coil into the second mode (or the third mode, in a three mode system).

In an alternative implementation, the primary coil is a litz coil consisting of a plurality of insulated wires, and the quality factor is controllable by selecting a number (or in other words, which) of the insulated wires through which an electric current passes during wireless charging or the receiving of sensor data. The primary coil may be operated in the first mode by passing an electric current through a first proportion of the insulated wires, and operated in the second mode by passing the electric current through a second, lower, proportion of the insulated wires. The first proportion may be substantially all of the insulated wires within the litz coil. The second proportion may be approximately 10% of the total number of strands.

It will be appreciated that a litz coil could be used with a damping resistor (without using different numbers of insulated wires to achieve the different quality factors), or the two implementations could even be combined so that variation in quality factor is achieved by way of a combination of both damping resistors (or other components which serve to modify the resistance of the coil circuit) and by using different proportions of the insulated wires of a litz coil.

The controller may be operable to determine a data transfer performance, and to control the quality factor of the primary coil in dependence on the determined data transfer performance. In this case, the quality factor of the primary coil may be tailored to the current transmission environment, which in the present application may vary significantly as a function of the relative position and orientation of the primary and secondary coils of the receiver device and the sensor device respectively, and external interference. In one example, the controller is operable to determine the data transfer performance during a quality factor adjustment phase carried out prior to the transmission of the sensor data from the sensor device and/or prior to the transmission of a signal from the receiver device to the sensor device. The data transfer performance may for example be based on a CQI—Channel Quality Indicator metric, or other metric of wireless communication quality.

Preferably, the sensor device is an implantable sensor device shaped and dimensioned for implantation in a body cavity for measuring conditions within the body cavity. The body cavity may be a uterus. The receiver device may be wearable, and the primary coil may extend around the body of the user when the device is worn. The wearable receiver device may be a belt, a bra, an item of underwear or a sanitary towel, or comprise a patch coil.

The primary coil may comprise a plurality of turns, each turn extending around the body of the user, and each turn being formed of a litz wire.

According to another aspect of the present invention, there is provided a receiver device comprising a controller, and a primary coil for wirelessly receiving sensor data from a sensor device having a secondary coil, the receiver device being operable to wirelessly charge the sensor device via electromagnetic inductive coupling between the primary and secondary coils;

wherein a quality factor of the primary coil is controllable; and wherein the controller is operable to control the quality factor of the primary coil to be higher when the receiver device is wirelessly charging the sensor device than when the receiver device is receiving sensor data from the sensor device.

According to another aspect of the present invention, there is provided a method of using a receiver device to wirelessly charge a sensor device using an inductive coupling between a primary coil of the receiver device and a secondary coil of the sensor device, and of wirelessly receiving sensor data from the sensor device at the receiver device via the primary and secondary coils, the method comprising:

controlling a quality factor of the primary coil to be higher when the receiver device is wirelessly charging the sensor device than when the receiver device is receiving sensor data from the sensor device.

The (adjustable) quality factor referred to within the present disclosure is the quality factor of the primary (receiver device) coil.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Figure 1:
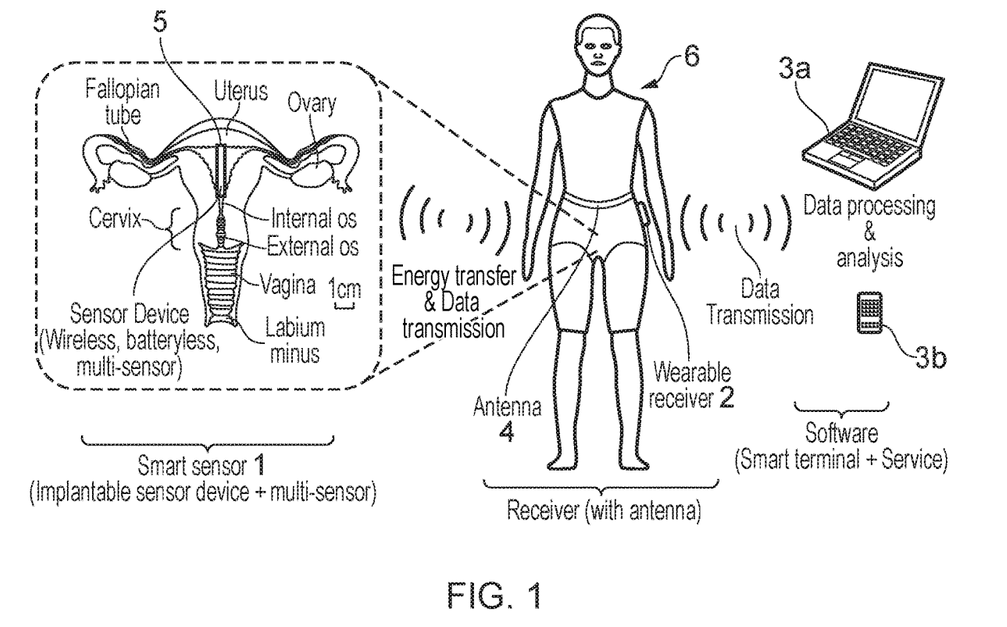
FIG. 1 schematically illustrates an intra-uterine monitoring system.

Referring to FIG. 1, a three-module structured multi-parameter in-vivo sensing platform for intra-uterine environment monitoring is shown. The platform comprises a smart sensor 1 (implantable sensor device, which is suitably shaped and dimensioned for implantation in a human uterus), an external, generally wearable, receiver 2 and monitoring software installed on suitable data processing hardware, such as a computer 3a or portable electronic device 3b. The smart sensor 1 is a fully implantable (within the uterus 5 of a human female body 6) sensor device incorporating multiple embedded biosensors (intended for measuring temperature, dissolved oxygen concentration (DOC) and pH). Temperature, DOC and pH are considered to be the three most important parameters to measure for this application because they maintain a homeostatic controlled balance of gases and acid-base which is vital to human life and reproduction. They are likely to determine the receptivity of the intra-uterine environment to an implanting embryo.

The smart sensor 1 is capable of wirelessly receiving power from and wirelessly transmitting data to the wearable receiver 2 which is located outside the body of a user, and worn by the user. As a result, the smart sensor 1 dispenses with the need for a battery and cables, and is of comparable size to the widely-used IUDs (intra-uterine devices) for contraception. This is important, because for implantation in the uterus, a device must meet strict size limits. Compared with intra-uterine devices (IUDs) widely used for contraception, battery-based sensors have been found to be too large to be used in the uterus. Moreover, designs based on a battery typically have limitations due to the physical size of the battery and short lifetime before the battery is too depleted to continue operating. Furthermore, there are potential risks from the toxic material of batteries.

The receiver 2 serves as a medium between the implantable sensor device 1 and the external data processing device running suitable software (and thus operating as a data analyser). In particular, the receiver 2 delivers energy to the sensor device and collects real-time information. An antenna 4 of the receiver 2 can be embedded into clothing and wired to the receiver 2. The software module is developed for in-vivo data uploading simultaneously to smart terminals or PC servers for post data processing and analysis. The software module consists of a set of monitoring software running on a PC or smart terminal which is designed to be a friendly user interface for data processing and system configuration. The positioning of the smart sensor 1 within the uterus is shown in FIG. 1. In particular, the smart sensor 1, which may typically have a generally elongate structure, is positioned substantially upright (vertical) within the uterus. As a result, the longitudinal axis of the smart sensor 1 is substantially vertical when the user is standing.

In this three-module structured system, the effectiveness of the wireless energy transfer and data communication between the smart sensor 1 and receiver 2 directly affect the usability of the intended system. An optimised design may not only result in better performance (that is, the robustness of the system to various different orientations (which differs from person to person) of the uterus, various sizes of user, and the daily activities of the user), smaller size, low power consumption and lower cost, but also improve end-user experience and clinical practise.

Figure 2:
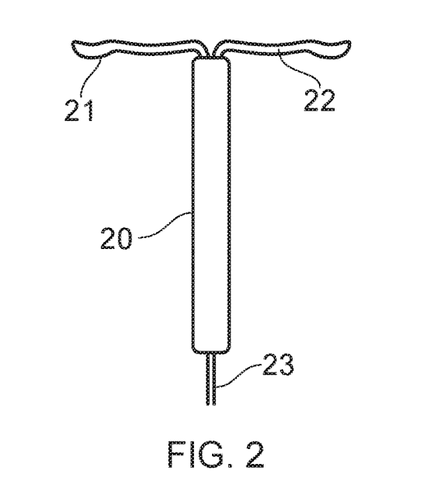
FIG. 2 schematically illustrates an implantable sensor device.

Referring to FIG. 2, an example structure for the smart sensor 1 is shown. In FIG. 2, a T-type smart sensor can be seen to comprise a body 20, a first arm 21, and a second arm 22. Once inserted into the uterus, the first and second arms 21, 22 help to retain the smart sensor 1 in place within the uterus. While in the present embodiment two arms are used, it should be understood that in other embodiments a single arm could be used, or more than two arms could be used. The body 20 may comprise a main circuit board (not shown) and an antenna (also not shown). Alternatively, the antenna may be fixed on the second arm 22. The main circuit board carries the sensors and the circuitry for temporarily storing electrical energy, controlling the smart sensor 1 in acquiring sensor data, and in transmitting the acquired sensor data to the wearable receiver device.

The sensor device orientation is vertical in the uterus, making it suitable for use with a receiver having a belt antenna or an antenna embedded in underwear. A cord 23 is used to assist with removal of the device from the uterus.

Figure 3:
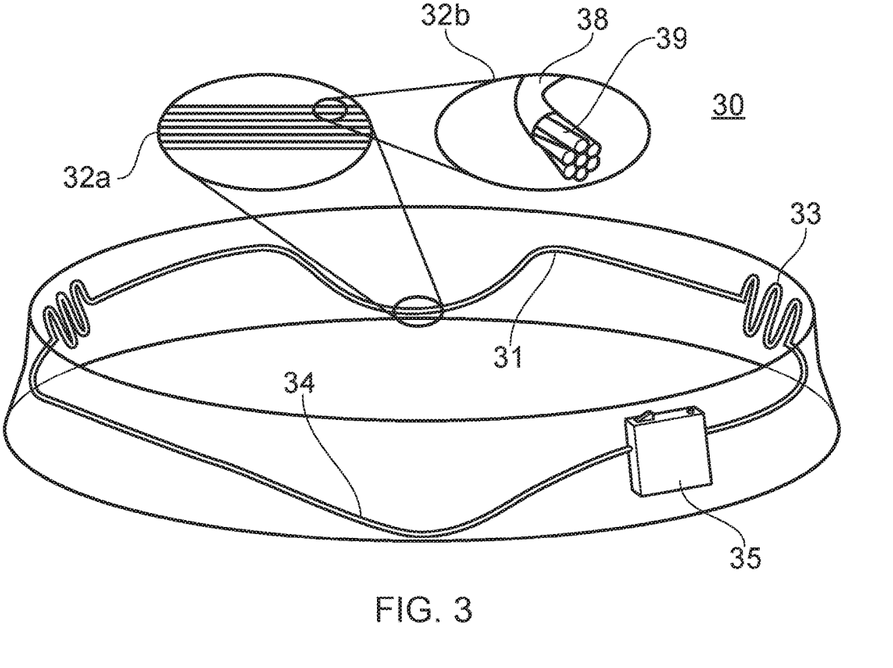
FIG. 3 schematically illustrates a wearable receiver device.

Referring to FIG. 3, a belt 30 is provided as a wearable receiver device, and comprises a complete coil 31 which extends around the belt, and which has a length longer than an intended waist size. The coil 31 is embedded within a partially elastic belt structure, which may be a composite structure of fabric panels and elastic supports, or may be a simple elastic material structure. The user is required to pass the belt 30 over their head, or over their feet in order to wear it, since the belt forms a continuous loop. The coil 31 comprises several turns (that is, a continuous current path extends about the belt, and thus the waist of the wearer, a plurality of times), as shown close up at 32a. A further close up view at 32b shows that each turn of the coil 31 is a litz wire 38, which comprises a large number (preferably tens or hundreds) of parallel connected enamelled (insulated from each other) thin wires 39. The significance of the litz wire will be explained in detail subsequently.

The coil 31 may extend in a generally linear manner about a substantial portion of the belt, with the exception of at first and second extendable regions 33 which are intended to be located to the side of the wearer, and a downwardly extending region 34 intended to be located to the front of the wearer. A further downwardly extending region is provided opposite the region 34, to the rear of the wearer. A receiver unit 35 (comprising a microprocessor and transceiver electronics) is removably mounted to the belt 30. The extendable regions 33 comprise a coil wiggle to permit elasticity. The belt itself is preferably elastic only within the extendable regions 33, since expansion of the belt elsewhere may result in stresses on the linear parts of the coil, leading to damage. The downwardly extending region 34 may extend downwardly to a certain level of groin contour which is preferably slightly lower than the uterus on the horizontal plane (by a few cm). The downwardly extending region to the rear of the belt/wearer may be smaller, for example extending downwardly by only a few CM.

Figure 4:
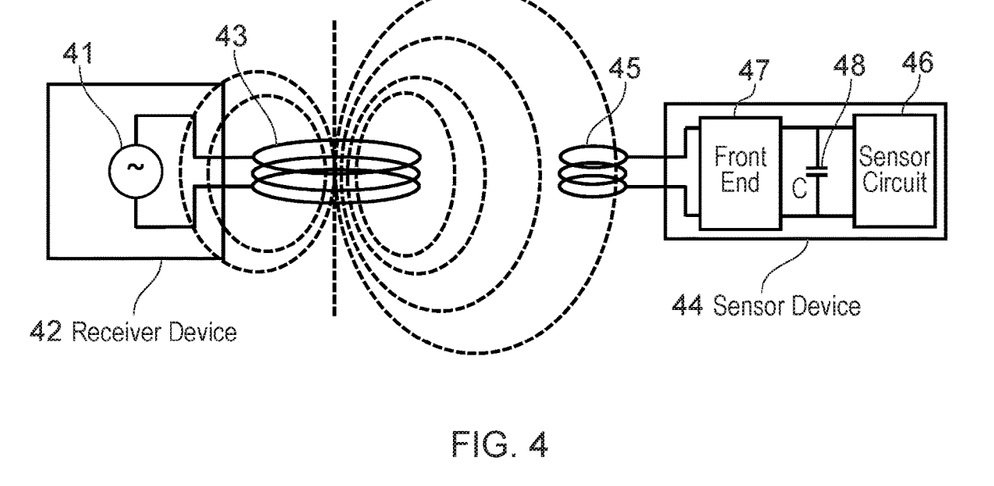
FIG. 4 schematically illustrates an inductive coupling between a sensor device and a receiver device.

Referring to FIG. 4, a sensor device/receiver device setup which illustrates the manner in which a receiver device 42 and sensor device 44 can be expected to communicate and transfer power is shown. In FIG. 4, electrical power, generated by an AC source 41, is transferred from the receiver device 42 to an inductively coupled sensor device 44 using the energy of the alternating magnetic field generated by the receiver device 42. Power transfer in FIG. 4 is achieved by the principle of magnetic induction, where both wireless power transfer to the sensor device 44 and communication between the two devices are achieved using the same nearfield magnetic induction link.

The receiver device 42 drives a primary coil 43 at low frequency to generate a magnetic field (in this case at a frequency of order 100 kHz). The sensor device 44 has a secondary coil 45 in the vicinity of the primary (receiver) coil 43, which is inductively coupled to the receiver coil 43 (via the magnetic field H). This results in an induced voltage across the sensor coil 45 which is then converted to energy by a front end 47 to power an integrated circuit 46 of the sensor device 44. More particularly, the front end 47 uses the energy received at the coil 45 to charge a capacitor 48, which can subsequently be used to power the sensor circuit 46. To allow high power transfer efficiency over distance, both the receiver 42 and sensor device 44 are preferably designed to operate their antenna circuits at the same resonant frequency.

The communication between the receiver device 42 and the sensor device 44 is achieved using the same pair of coils 43, 45 as for powering the sensor device 44. When the receiver device 42 or the sensor device 44 manipulate an applied voltage to change the amplitude, frequency or phase of the voltage on one side, the other side will detect a similar change via the inductive link between the two devices. The message is encoded in this change, and how fast the message can be sent, or the data rate, is dependent on the bandwidth of this inductive link. Any form of modulation (amplitude, frequency or phase) will generate sidebands in the frequency domain, which makes the modulated signal difficult or impossible to detect if the frequency spectrum of the modulated signal does not fall wholly or substantially within the bandwidth of the inductive link. In the present embodiment, messages transmitted, via the inductive link, from the receiver device 42 to the sensor device 44 may be command messages to trigger the sensor device 44 to take sensor readings (for example), while the messages transmitted, via the inductive link, from the sensor device 44 to the receiver device 42 may be sensor data generated by a pH sensor, temperature sensor or dissolved oxygen sensor (for example), or status messages indicating the current status (e.g. power level) of the sensor device 44.

When an electric current runs through a conductor (such as when the receiver device of FIG. 4 applies a voltage to the coil circuit driving the coil antenna 43), a magnetic field is generated around the coil antenna in the orthogonal plane. The magnetic field strength at a particular distance from the coil antenna is associated with the amount of current running through the conductor and the distance from the coil. The greater the current or the closer the measurement point to the coil, the stronger the magnetic field strength and vice versa. In particular, a receiver coil having a relatively larger diameter can project higher magnetic field strength at greater distances, whereas a coil having a relatively smaller diameter generates a stronger field strength at shorter distances. In other words, for the same driving circuit and sensor coil, at relatively short distances a small receiver coil performs best, whereas at relatively long distances a large receiver coil performs best, with there being a cross over region where the coils have a similar performance.

Figure 5:
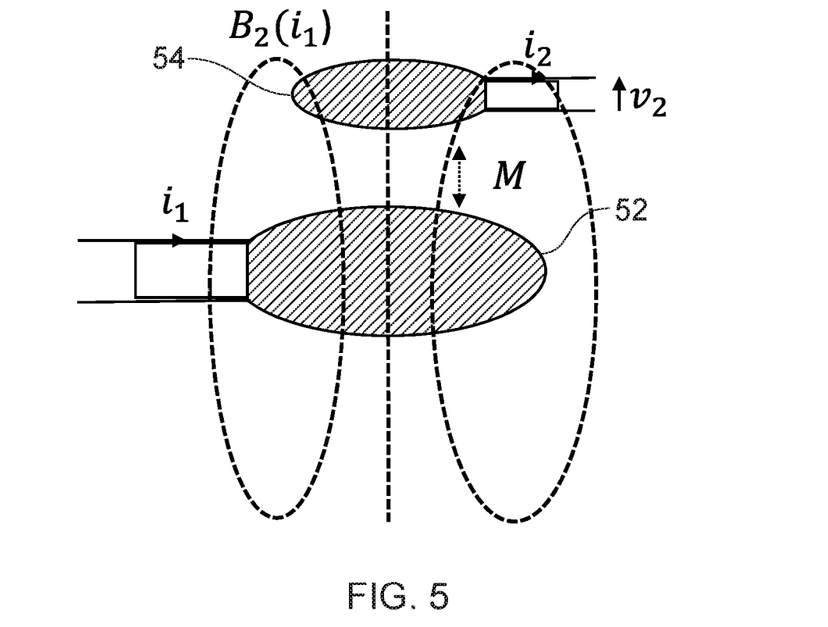
FIG. 5 schematically illustrates how the inductive coupling gives rise to a voltage at the sensor device.

Referring to FIG. 5, a receiver generates an electric current $i_1$ which passes through a loop of the receiver coil 52 thereby generating magnetic flux (magnetic field $B_2(i_1)$) which enters a loop enclosed by sensor device coil 54.

According to Faraday's law/Lenz's law, a change in the total flux linkage introduces an electromotive force (voltage) opposing the change. It is the change of the total flux linkage that induces the voltage, which is why the source of the magnetic field must be generated by an AC signal, thus an alternating magnetic flux is generated by the receiver coil and picked up by the sensor device coil. As shown in FIG. 5, when the loop of the receiver coil 52 is driven by an applied current $i_1$, the generated magnetic flux is picked up by the area enclosed by the loop of the sensor device coil 54, and hence a voltage $v_2$ is developed across the sensor device coil 54. This voltage is used to power the sensor device (for example by charging a capacitor, so that the sensor device can operate while a magnetic field is not being applied).

Given that the dimensions of both coils and the distance between the coils is fixed for this application (both of these factors affect the mutual inductance M), if the current $i_1$ is increased, the magnetic field $B_2$ also increases, resulting in an increase in the voltage $v_2$. In order to increase $i_1$, the coil is made to work in resonance thus the impedance resulting from the inductance of the coil is cancelled by the impedance of a series resonant capacitor. In this case, the impedance is purely resistive from the resistance of the coil itself and other small resistances within the resonant circuit. As discussed elsewhere, the resistance of the coil may be decreased by using litz wire, thus improving the quality factor, Q. At a high value of Q, the resistance R of the coil 52 is lower, and the current $i_1$ is higher, resulting in a stronger field $B_2(i_1)$ being generated and thus a larger voltage $v_2$ being induced in the sensor coil 54.

A coil antenna may be approximated by stacking multiple loop antennae. When the current running through the coil is a static DC current, a static magnetic field is generated. When an AC signal is driving the coil, the magnetic flux generated is also alternating. This change in the magnetic flux is picked up by the driven coil itself, thus inducing a voltage opposing to this change.

In a two-coil system, the receiver coil (for example the coil 52) generates an alternating magnetic field, which induces a voltage opposing this change in the sensor device coil (for example the coil 54). This induced voltage in the sensor device coil then generates a magnetic field coupled back to the receiver coil, inducing a voltage in the receiver coil, essentially, acting like an additional inductor to the receiver coil. This magnetic induction link can be described by the mutual inductance, which depends on the dimensions of and the distance alignment (orientation) between the two coils. If both the coils are in a given geometry, the mutual inductance is changed by the distance between the two coils. A coupling coefficient k may be used to describe the quality of the induction link between the two coils. When k=0, the two coils are completely decoupled. When k=1, the two coils are fully coupled. In practice, k will fall between these two extremes, with a higher value of k representing a higher degree of inductive linkage. To give examples, a transformer is almost 100% (k=1) coupled by linking the flux of two coils via a highly permeable iron core, whereas a typical RFID system (analogous to the present application) is only coupled 3-5% as they are linked by free space/air.

For a given pair of inductively linked coils, the sensor device will receive the highest voltage (power) if the receiver coil current $i_1$ is at its highest and the mutual inductance between the two coils is high (better coupling). As discussed above, it is possible to increase the mutual inductance by moving the two coils closer together, whereas if the distance is limited by the application, the power delivered can be improved by increasing the amount of current passed through the primary coil.

Figure 6:
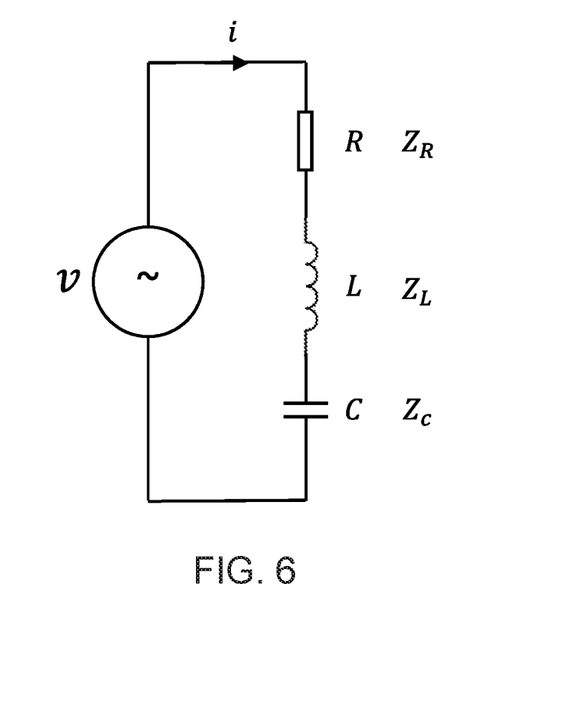
FIG. 6 schematically illustrates the receiver device coil circuit represented as a series RLC (resonant) network.

An equivalent circuit of the receiver device coil may be considered as a series RLC (resonant) network. Referring to FIG. 6, an equivalent circuit of a standalone receiver device coil is shown. The receiver device coil circuit may be considered as a voltage source (driving circuit) v, a resistor R which models the ohmic resistance in the coil, the receiver coil itself which is an inductor L, and a resonance capacitor C. The LC network is tuned to operate at its resonant frequency.

The alternating current in the receiver device coil is equal to the voltage divided by the impedance of the RLC network. At resonant frequency, the impedance $Z_L$ of the inductor and capacitor $Z_C$ cancel each other out. Therefore, the impedance of the series resonant circuit is purely resistive and at the minimum; the amplitude of the coil current and thus the magnetic field it generates is at its peak. This peak value is determined by the voltage driving the coil, and the resistance of the RLC network at resonance (at frequency $f_{res}$).

$$f_{res} = \frac{1}{2\pi\sqrt{LC}}$$

Figure 7:
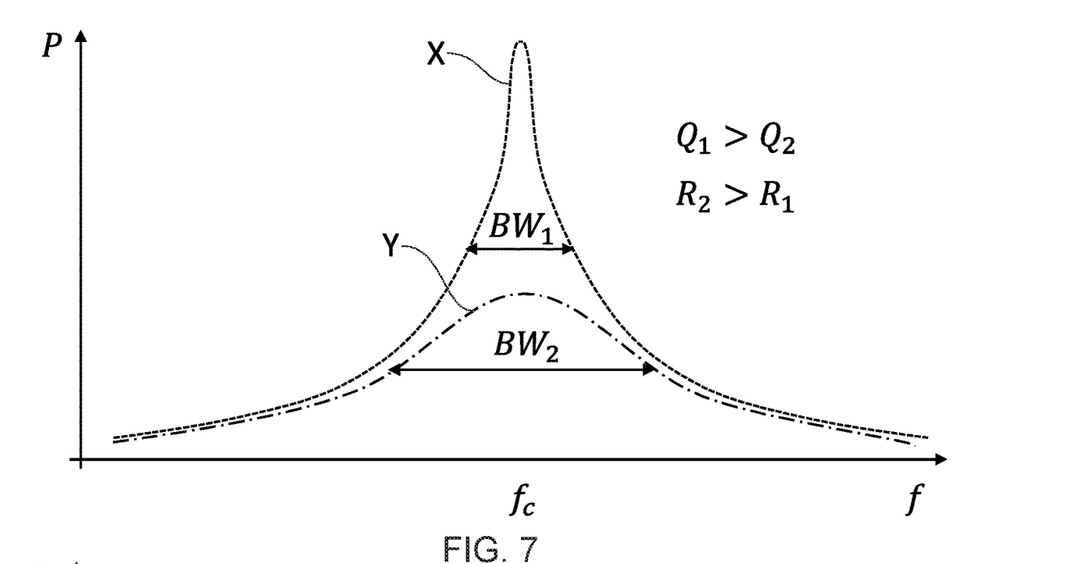
FIG. 7 schematically illustrates a relationship between transmitted power and frequency for two RLC (resonant) transmission circuits having different levels of resistance through the resonant circuits of the coil, and with the differing bandwidths of different RLC circuits with different Q factor being evident.

It is possible to increase the peak current by increasing the driving voltage. However, this would translate into high power bulky circuitry and battery, and the energy will be wasted as heat in the resistor. Alternatively, the total resistance of the system at the resonant frequency may be reduced, making the system more efficient. In FIG. 7, a relationship between transmitted power and frequency for two different resonant circuits, circuit X and circuit Y, with the same resonant frequency are shown. Both circuits result in a bell curve centred on a central frequency $f_c$. The second of the two circuits, circuit Y, has a larger resistance $R_2$, than the resistance $R_1$ of the first of the two circuits, X. It can be seen that the receiver coil power at resonant frequency has a much larger peak in comparison when the resistance is lower. This is ideal for wireless power transfer, provided both the receiver device and sensor device are operating at the same resonant frequency.

However, it can also be seen from FIG. 7 that the percentage current drop with respect to its peak current value is much more severe for the low resistance coil circuit X than for the high resistance coil circuit Y when the driving frequency is shifted away from the resonant frequency by the same amount. Thus, although the low resistance coil circuit is better in an ideal world, the high resistance coil circuit is more robust to detuning.

The peak width or band width (BW) of a receiver coil is defined as the maximum frequency shift for which the peak power at resonant frequency has reduced to half, or when voltage/current is reduced to $\sqrt{2}/2$ of its peak value. The quality factor Q of a receiver coil can be defined as:

$$Q = \frac{\omega_0 L}{R}$$

Where $\omega_0$ is the resonant frequency and R is the total resistance and L is the inductance of the receiver coil. It is clear that it is possible to increase the quality factor by decreasing the total resistance of the receiver coil.

The quality factor can also be related to the band width and resonant frequency $f_{res}$:

$$Bandwidth = \frac{f_{res}}{Q}$$

The higher the quality factor, the higher the amplitude of current running through the coil at resonance. It is also apparent the higher the quality factor the receiver coil has, the lower the band width it has. For a receiver coil, Q factor is related to its ability to project power over distance, whereas band width is important in describing the receiver coil's sensitivity to a shift in driving frequency, which is closely related to communication effectiveness.

Given that reducing total resistance of the receiver coil can improve the Q factor thus performance in wireless power transfer, it is important to know the resistance of the coil:

$$R_{total} = R_{dc} + R_S R_p + R_r$$

Where $R_{dc}$ is the DC resistance of the coil, $R_S$ is the resistance due to skin effect, $R_p$ is resistance due to proximity effect, $R_r$ is radiation resistance. For the low frequencies of interest in this application, and assuming that the coil is constructed properly (see discussion of Litz coil below), it is possible to ignore $R_p$ and $R_r$.

A receiver coil or inductor is essentially a long wire, thus from the following equation one can calculate the DC resistance:

$$R_{dc} = \frac{\rho l}{A}$$

To reduce the DC resistance it is possible to use more conductive material such as silver to reduce resistivity ρ (but this is expensive), reduce the length l (not viable because length of wire is related to inductance), increase the cross sectional area A or diameter of the wire (possible but thicker wire increases weight of the wearable system). Thus, it is possible to increase the diameter of the wire used in the receiver coil moderately in an effort to reduce the $R_{dc}$. However, as the frequency of the signal passing through a conductor increases, the electrons tend to flow on the surface of the conductor. The current density of the conductor decays exponentially as the depth increases in a conductor. At the present frequency of approximately 100 kHz, the skin depth is around 0.178 mm. This means the maximum effective diameter of wire which is used is 2×0.178 mm and the remainder of the wire (central part) is not utilised.

To mitigate the skin effect, Litz wire can be used. Litz wire is a collection of thin wires stranded together and connected in parallel to reduce AC resistance associated with the skin effect which occurs at high frequency. Each of the wires are insulated with an enamelled layer and joined together at the terminals. The diameter of each strand of wire is determined by the working frequency, in the present case the wire is preferably smaller than 2×0.178 mm in diameter. This way, the overall diameter of the wire can stay unchanged, while each strand of wire is carrying current at optimal capacity, such that overall the effective resistance is reduced significantly.

By using Litz wire instead of a solid wire coil, it has been possible to improve the quality factor from around 25 to around 800 (note that the specific number depends on application and design). However, a setup with Q=80 has been used to improve the comfort of a wearable coil. The improvement of the receiver coil has extended the working range and angle significantly. The high efficiency coil has reduced the size of the electronics and battery by 80%, reducing cost by more than 50%.

However, as expected the increased Q factor has reduced the band width, which potentially affects the communication distance of the device. Specifically, a problem has been discovered where the receiver device can communicate with the sensor device at a longer range, whereas at very close range, the communication may fail. At close range, the powering of the device is not a problem, however the receiver coil can no longer detect the message from the sensor device correctly, indicating a problem with the communication. In the following paragraphs, the communication is discussed in more detail.

Figure 8:
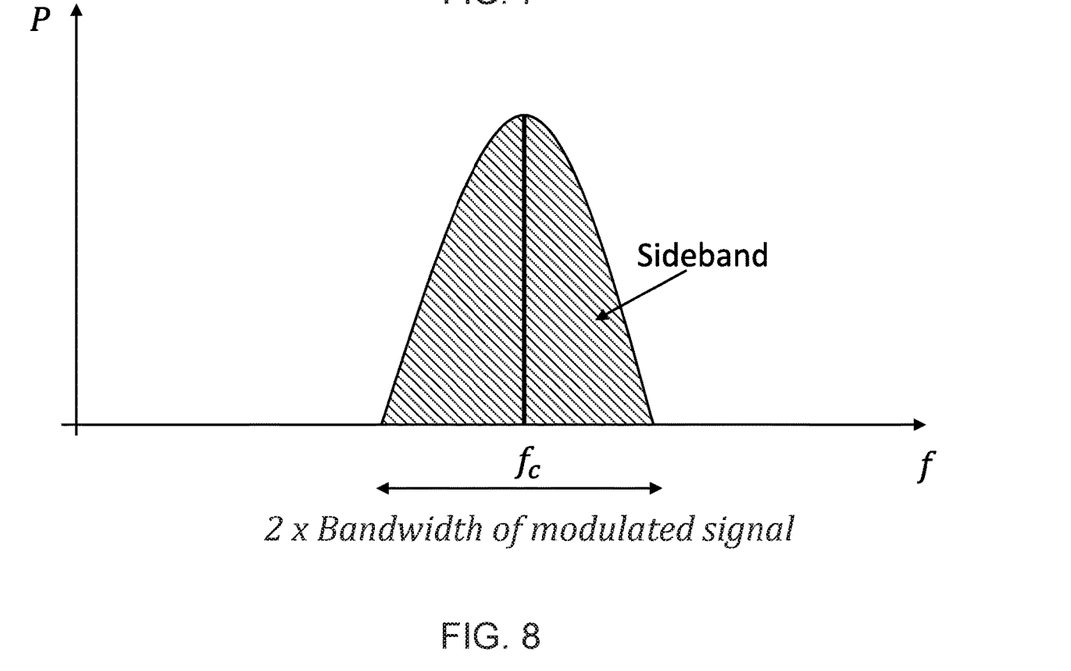
FIG. 8 schematically illustrates sidebands of a modulated signal.

Any periodic signal can be reconstructed with combinations of sine waves and cosine waves in different frequencies/amplitude/phase. An RFID system or generic telecommunication system usually communicates via the modulation of a periodic electromagnetic signal. Modulation of a signal basically means to convey a message by manipulating the amplitude, frequency or phase of a carrier signal. This modulation procedure, or the manipulation of these parameters will always cause a change in the frequency domain. In one example, a modulation method which can be used is Quadrature Phase Shift Keying, which uses a small signal to tweak the phase of a carrier signal, the information being contained in this small signal. As a result, in the frequency spectrum the components of this small signal will be seen to surround the central carrier frequency. The faster this small signal is, the faster the communication link is, and the wider the window within which this signal appears on the frequency spectrum (that is, it requires a larger bandwidth). Another example, in this case of a frequency spectrum of an amplitude modulated signal is shown in FIG. 8. Here, the sideband contains the message signal spread around the central carrier frequency. In this case the carrier signal is also used to provide power to the sensor.

Recalling FIG. 7, if the Q factor of the receiver coil is too high, the bandwidth will be too small, thus the available "window" where the modulated signal can pass through is too narrow. In particular, some of the lower frequency components will be attenuated whereas some of the higher frequency components closer to the resonant frequency of the coil will be amplified. Essentially the frequency spectrum of the signal may become sufficiently distorted that the reconstructed signal cannot be detected properly at the demodulator circuit. This is the point where the communication will fail. One reason why a system employing a Litz coil fails to work at short distance, could result from the fact that mutual inductance of the sensor device is significant at close range, shifting the resonant frequency/frequency response of the receiver coil slightly. However, because of the high Q receiver coil, any shift in frequency could produce a significant drop in voltage level detected, thus shifting the sidebands of any modulated signal out of the receiver coil bandwidth, resulting in failed communication.

It will therefore be appreciated from the above that the present application requires a high-Q coil to improve wireless power transfer performance, but that the use of a high-Q coil decreases communication performance. This makes it difficult to use a single coil at the receiver device both to provide power to the sensor device, and also to receive data from the sensor device.

In order to overcome this problem, the present technique modifies the Q-factor of the receiver coil depending on an operating mode, such that the wireless power transfer is carried out with the receiver coil operating with high Q, whereas the communication is carried out with the receiver coil operating with a low Q.

Figure 9:
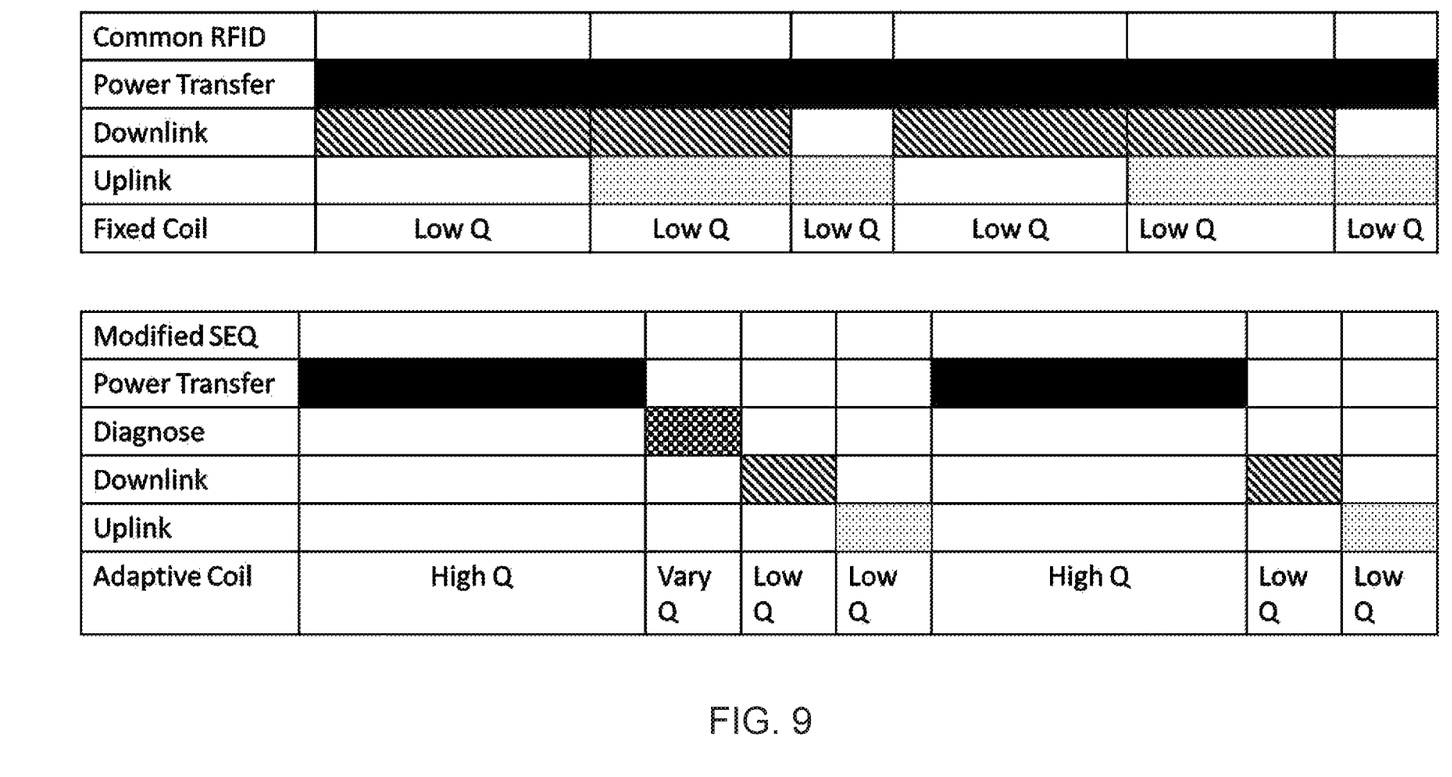
FIG. 9 schematically illustrates an example sequential communication/power transfer schedule for implementing the present technique.

A battery-less communications system could utilise several different communication protocols. Full-Duplex and Half-Duplex protocols provide wireless power transfer continuously and simultaneously with communication. In these systems it is not possible to change the Q factor of the coil without affecting both wireless power transfer and the communication. Referring to FIG. 9, a comparison is provided of a common RFID power transfer and data communication schedule using a full duplex protocol with a modified sequential power transfer and data communication schedule according to a new protocol developed for use with the present technique. In FIG. 9, data transfer from the receiver device to the sensor device is termed down-link, while data transfer from the sensor device to the receiver device is termed up-link. The new protocol uses a diagnose (quality factor adjustment) period in advance of at least a first data transfer operation.

In the full duplex protocol, it can be seen that power is transferred continuously, and that both downlink data transfer and uplink data transfer is carried out in parallel with power transfer. Moreover, downlink data transfer and uplink data transfer are also carried out in parallel with each other. Due to the fixed quality coil, all power and data transfers are carried out at a relatively low quality factor in order to be able to achieve both power transfer and data communications at the same time.

In contrast, in the modified sequential protocol, power transfer is not carried out at the same time as either downlink or uplink data communications. Moreover, downlink and uplink data communications are not carried out at the same time. Instead, power transfer and communications are carried out sequentially. In FIG. 9, a diagnose phase is also provided, although this is an optional feature provided specifically for adaptive quality factor control, and can be dispensed with if it is only necessary to modify the quality factor in accordance with which of a power transfer, uplink and/or downlink is being carried out. The diagnose phase is used to determine a quality factor required to support downlink data communications and/or uplink data communications, and will be described further below with reference to FIG. 10.

Returning to FIG. 9, the final row of the modified sequential protocol defines the quality factor used for each phase. In particular, considering the phases from left to right, during a power transfer phase, a high (maximum) quality factor is used. Then, during a diagnose phase, the quality factor is varied to determine appropriate quality factor(s) for downlink and/or uplink data communications (further details thereof being provided below). Then, during a downlink phase, a low quality factor (as optionally determined during the diagnosis phase) is used. Then, during an uplink phase, a low quality factor (as optionally determined during the diagnosis phase) is used. The quality factors used during uplink and downlink may be the same, or different. Where different, the quality factor used during downlink will generally be higher than the quality factor used during uplink (but generally lower than that used during power transfer).

Following the uplink data communications phase, a new power transfer phase commences, followed by new downlink and uplink data communication phases. The diagnose phase in this case is not repeated every cycle, since it is assumed that the determination made, during the initial diagnosis phase, of the most appropriate quality factor(s) to use will remain sufficiently accurate over multiple cycles. The diagnose phase may in some embodiments be carried out on a periodic basis (for example, every few seconds, or milliseconds, and in other embodiments be carried out only the first time that the receiver device and the sensor device start communicating following a period of inactivity. While in FIG. 9 a single diagnosis phase is carried out immediately before the downlink phase, it will be appreciated that it could be carried out at another time during the power transfer and data communications schedule. Moreover, the diagnosis phase could be separated into two parts—a first part (preferably immediately before the downlink phase) for determining a suitable quality factor to use for the downlink, and a second part (preferably immediately before the uplink phase) for determining a suitable quality factor to use for the uplink.

Variations on the modified protocol include (a) downlink and uplink data communications are carried out at the same time, and/or (b) power transfer and downlink data communication are carried out at the same time. Note that options (a) and (b) cannot be achieved at the same instant in time without breaching the requirement to not transfer power and communicate on the uplink at the same time, but could in principle be achieved at different times in the same schedule. In particular, the most substantial conflict is between power transfer and uplink data communication. This is because, due to the relatively small size and low power level of the sensor device (secondary) coil, the voltage signal generated by the uplink data signal is very small compared with the voltages used in the power transfer. In contrast, the conflict between downlink and uplink data transfer is substantially less severe, and so concurrent operation may be possible. Similarly, the downlink data transfer can tolerate a relatively high quality factor, and so a compromise between power transfer and downlink quality factor may be possible, making concurrent power transfer and downlink communication possible.

It will also be appreciated that the particular order of the power transfer, diagnosis, downlink and uplink phases need not be that shown in FIG. 9—these may be carried out in a different order (although the diagnosis phase, where present, should be in advance of, but not necessarily immediately before, the downlink and/or uplink phase which it is to determine the quality factor for).

Figure 10:
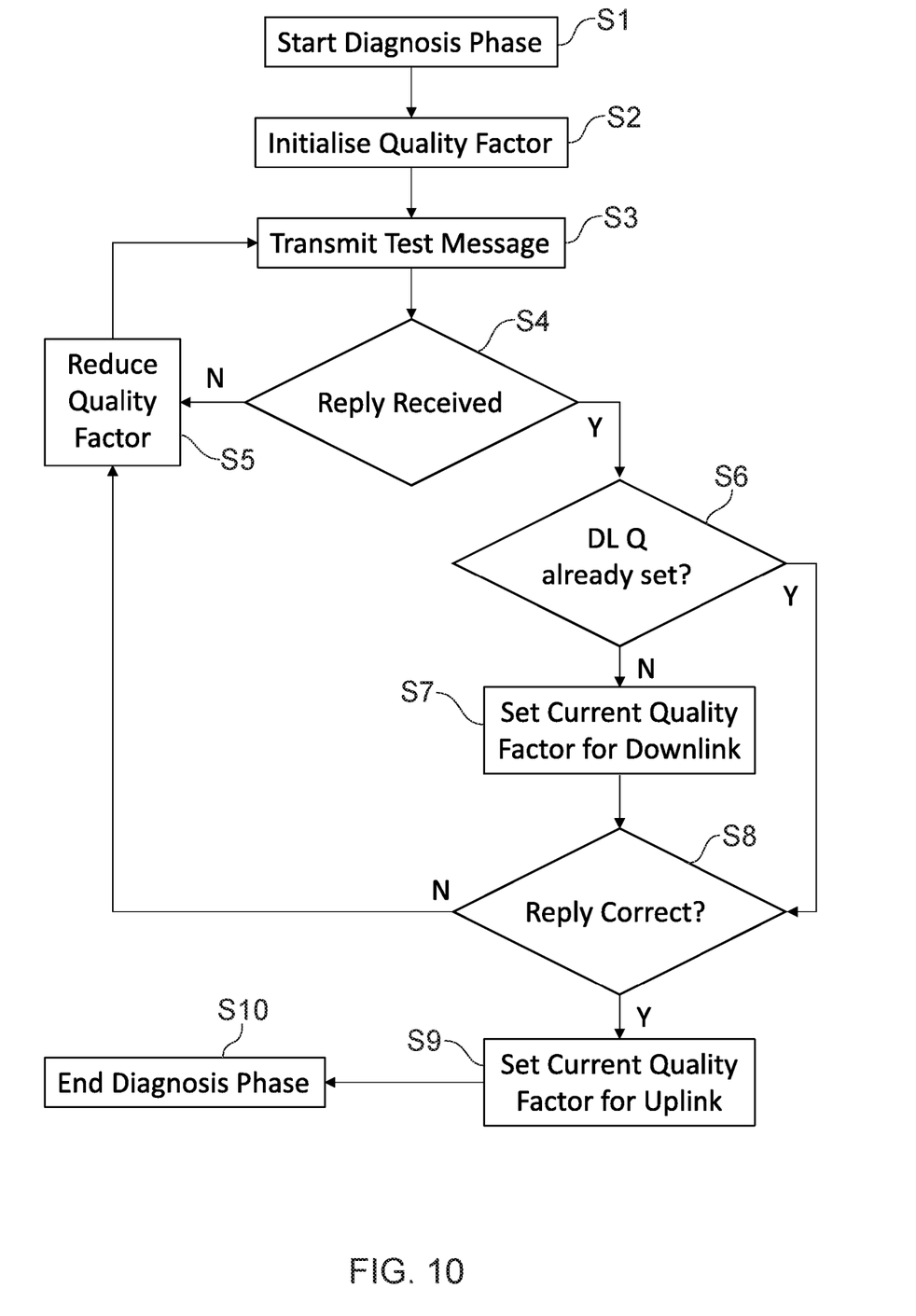
FIG. 10 is a schematic flow diagram illustrating an adaptive Q factor control method.

Considering now FIG. 10, a flow diagram is used to set out an example diagnosis phase. At a step S1, the diagnosis phase starts. At a step S2, the receiver coil initialises the quality factor of the coil to a predetermined start value. The start value may be the quality factor for power transfer, or another value found to be a best case for transmitting data on the downlink. At a step S3, a test message is transmitted from the receiver device to the sensor device via the inductive link. If the quality factor is too high for the test message to be correctly (without an unacceptable degree of distortion/an error rate which is too high) received by the receiver device via the inductive link, then the sensor device will not respond. At a step S4, the receiver device determines if a reply has been received. If not, then the quality factor is reduced at a step S5, and the process returns to the step S3, where another test message is transmitted at the reduced quality factor. This process continues until a reply is determined to be received at the step S4. Then, at a step S6, it is determined if a quality factor for the downlink has already been set (for this cycle of the diagnosis phase). If not, then at a step S7 a current quality factor is set for the downlink. The quality factor set at the step S7 is based on the quality factor most recently set at the step S3, but preferably reduced by a small margin to improve the reliability of the downlink. The process then progresses to a step S8. If at the step S6 it is determined that a quality factor for the downlink has already been set, then the step S7 is skipped, and the process moves directly to the step S8.

At the step S8, it is determined by the receiver device whether the reply received from the sensor device has been correctly received. In the present example, "correctly received" may mean that a received message has been fully and correctly decoded (that is, decoded and has passed any error detecting algorithms (for example a CRC (cyclic redundancy check) or any other form of popular algorithm)). In other examples, "correctly received", may mean that the error rate in the received reply message is sufficiently low (below a threshold error rate). If the reply message has not been correctly received, then the process reverts back to the step S5, where the quality factor is further reduced. The steps S3, S4, S6 and S8 will then be repeated (the step S7 will generally not be repeated once it has been triggered once) successively until the step S8 is answered in the affirmative. If it is determined, at the step S8, that the reply message is correct, then at a step S9 a current quality factor is set for the downlink. The quality factor set at the step S9 is based on the quality factor most recently set at the step S3, but preferably reduced by a small margin to improve the reliability of the uplink. Following the step S9, the diagnosis phase then ends at a step S10.

It will be appreciated that an alternative process could be used in which test messages are sent repeatedly with successively lower quality factors until a reply is received (to set the downlink) or understood (to set the uplink), and then the quality factor is increased again (but in smaller steps) until a reply is no longer receiver or understood.

It will be appreciated from the above that the present embodiment uses a sequential communication scheme, where the energy transfer and up-link (and optionally downlink) are separated. The sensor device has a small capacitor that stores energy required to operate a microcontroller (MCU) and transmission circuit. The total separation of charging phase and communication phase provides a foundation for the active and/or adaptive damping of the receiver coil.

Figure 11:
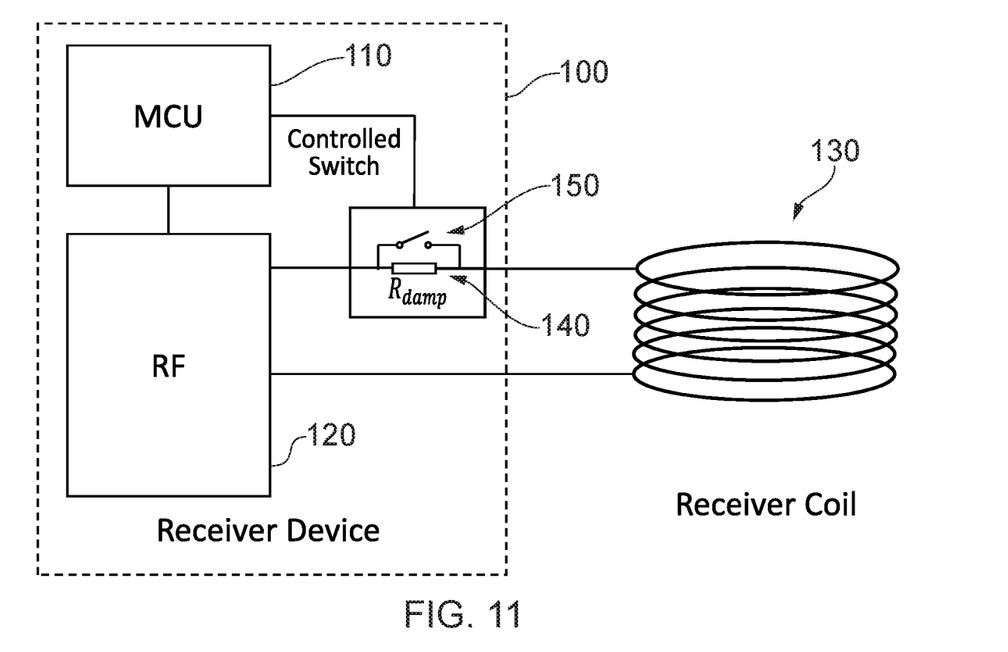
FIG. 11 schematically illustrates a receiver device coil and control circuit in which a resistor is switched into/out of the coil circuit in order to modify the quality factor.

Referring to FIG. 11, an example implementation of a receiver device 100 utilising active damping is shown. In the interests of clarity and brevity, only those components relevant to the present invention are shown. In practice, other components of the wearable receiver 2 described with reference to FIG. 1, would be present. The receiver device 100 comprises an MCU 110, which controls the operation of the receiver device 100, a transceiver (RF) unit 120, for applying an electric current/voltage to a receiver coil 130 to transfer power and/or data to the sensor device, and for detecting a modulated signal received at the receiver coil 130 from the sensor device. The receiver device 100 also comprises a damping resistor 140 and a switch (digital gate) 150. The damping resistor 140 is used to change the resistance of the receiver coil circuit. In particular, the switch 150 can be closed under the direction of the MCU 110 to short circuit the damping resistor 140 so that the resistance of the receiver coil circuit is low. The switch 150 can be opened under the direction of the MCU 110 so that the damping resistor 140 is in series with the receiver coil 130, with the result that the resistance of the receiver coil circuit will be relatively high. In particular, by gating the resistor 140 in-series with the high-Q receiver coil during a communication phase, it is possible to temporarily reduce the quality factor of the receiver coil, thus allowing adequate bandwidth for the communication to take place. When operating during a charging phase, the gated damping resistor 140 is removed from the circuit. The MCU 110 controls the timing with which the switch 150 is opened and closed, such that the quality factor changes are synchronised with charging and communication modes.

FIG. 11 shows a receiver device 100 capable of supporting two quality factors, one associated with power transfer and another associated with data transmission (reception and transmission). In an alternative implementation, data transmission and reception utilise different quality factors. In particular, two resistors are provided in parallel. In this case, by selecting between the two resistors (or selecting between using one or both of them), it is possible to select between two different quality factors in addition to the (high) quality factor associated with short circuiting both resistors. In this case, one of the two lower quality factors is associated data transmission from the receiver device to the sensor device, while the other of the two lower quality factors is associated with data reception from the sensor device. In this case, there would be three modes, carried out sequentially, a power transfer mode (high Q factor), a data reception mode (low Q factor A) and a data transmission mode (low Q factor B). It will be appreciated that one of Q factor A and Q factor B could be achieved by gating one of the resistors into the coil circuit, while the other of Q factor A and Q factor B could be achieved by gating both of the resistors into the coil circuit. It will further be appreciated that a greater number of resistance/Q factor levels may be provided, if required by the application.

Figure 12:
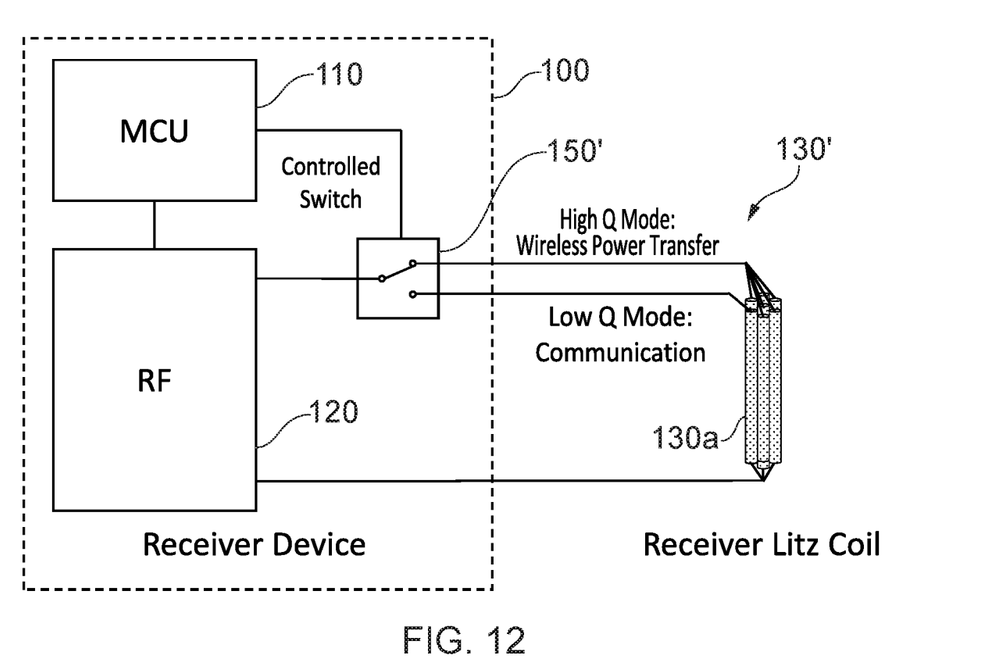
FIG. 12 schematically illustrates a receiver device litz coil and control circuit in which different number of strands of the litz coil are used to modify the quality factor.

It is also possible to modify the quality factor of the receiver coil in other ways (instead of or as well as by placing a damping resistor in series with the coil). For example, where the receiver coil is a litz coil, the resistance of the receiver coil can be adjusted by using different numbers of individual strands of the litz coil depending on whether the receiver device is operating in a communication mode or a power transfer mode. This is illustrated in FIG. 12, in which like parts compared with FIG. 11 are denoted by common reference numerals, and will not be described further. In FIG. 12, when operating in the power transfer mode, an electric current is passed through a greater number of the strands in the litz coil, to provide a high quality factor to maximise power transfer, while when operating in the communication mode, the electric current may be passed through a smaller number of the strands in the litz coil, thereby increasing the resistance of the connected litz coil, thereby reducing its quality factor, and thus improving its sensitivity to picking up on a modulated signal transmitted by the sensor device. In FIG. 12, a selector 150' selects between the use of a first group of strands 130a of a litz wire coil 130', and the use of a second group of strands (all the remaining strands of the litz wire coil 130'). It will be appreciated that, with more complex connectivity and switching circuitry, the selection could be between all of the strands, and a subset of the strands (that is, some strands would always be used, while other strands would only be used at the higher quality factor(s)).

In one example, the subset (or smaller number of strands) may be approximately 10% of the total number of strands (or of the larger number of strands). As a very rough approximation, the resistance can be assumed to be inversely proportional to the percentage of strands used, and the quality factor Q can be assumed to be proportional to the percentage of strands used. Accordingly, for the same configuration of coil, if the litz wire comprises 100 strands which give a quality factor Q of 120, using only ten of the strands could be expected to result in a quality factor Q of approximately 12.

The characteristics of Litz wire are defined by many different parameters, and they can be formed by various methods of construction. Depending on application, the number of strands may for example be between 50 and 200, and the diameter of each strand may be between 0.04 mm and 0.36 mm (for a frequency in the 100 kHz range, while if a different frequency range is used, thicker strands can be used but the flexibility of the wire decreases mechanically making it less suitable to use in a belt or undergarment, but potentially acceptable if used as a patch).

As with the use of two different resistors, the litz coil implementation of Q factor modification could also provide for multiple levels. For example, a high Q factor could be achieved by using all wires within the litz coil, while a first low Q factor could be achieved by using (say) 50% of the wires within the litz coil, and a second low Q factor could be achieved by using (say) 25% of the wires within the litz coil. A greater number of levels could be provided, if appropriate.

The present technique uses active damping of the receiver coil. It will be understood that the system uses the same coil to both transfer power to the sensor device, and communicate (bidirectionally) with the sensor device. The coil is operated in a high Q mode to project power over distance, and is operated in a low Q mode to allow sufficient bandwidth for communication. A sequential charging and communications procedure is used in which a charging phase and communication phase (at least the uplink, and preferably the downlink also) are separate. The sensor device is battery-less but has an MCU and storage capacitor. Electrical power stored in the storage capacitor is used both to take sensor measurements and to transmit a signal via an antenna on the sensor device.

As discussed above, particularly with reference to FIG. 9, the present technique can also provide adaptive damping. In this case, the Q factor or the receiver coil is not set solely as a function of mode (power transfer or data communication), but may also be set in response to the current performance or operating environment of the receiver device and sensor device. In particular, the coupling between the primary and secondary coil, and thus the data transmission performance, is sensitive to many factors including the relative positioning and orientation of the two coils and external interference. Accordingly, it may be desirable to adapt the quality factor in dependence on the data reception quality at the receiver device. In one example, the receiver device may have an initialisation, or diagnosis, phase as discussed in FIG. 9, for example prior to the transmission of sensor data from the sensor device to the receiver device. During this phase, the receiver device measures a signal quality, for example in the manner described in FIG. 9, or by measuring a test signal transmitted from the sensor device In another example, the receiver device may determine that a communication has failed (for example based on an expected message from the sensor device not being received), and trigger a retransmission with the receiver coil operating at a different quality factor. For example, a transmission from the receiver device to the sensor device might be expected to trigger an acknowledgement message from the sensor device. If such an acknowledgement message is not received, the original transmission could be retransmitted, but with the receiver coil being adapted to use a different (higher or lower) quality factor. Similarly, if an expected transmission from the sensor device to the receiver device is not received (this might be a scheduled delivery of sensor data), then the receiver device may modify the quality factor of the receiver coil and transmit to the sensor device a request for it to retransmit. These retransmission protocols need not necessarily be predicated only on the basis of an absent communication, but may be predicated on a communication which contains an unacceptably high error rate.

In one example, the voltage level of the carrier frequency of the uplink signal could be evaluated. If the device is too far away, the carrier signal voltage will be low, which would indicate that the sensor device may not be receiving sufficient power, requiring an increase to the quality factor Q. However, if the voltage level of this carrier signal is high but the message cannot be understood, this may be because the sideband is being attenuated too much, requiring a decrease in the quality factor Q.

It will be appreciated that the adaptive quality factor may be achieved by way of using a plurality of different quality levels, achieved either using multiple resistors, or different subsets of litz wires, or any other method of modifying the quality factor.

Embodiments of the present technique dynamically modify the resonant model of the coil circuit for power or communication of an inductively-coupled system. Most of the inductive coupling parameters (such as coil dimensions and the distance between them) are physical. These parameters are constrained in the case of the present sensor device and receiver, and so the electrical properties of the coil are adjusted instead.

While the various techniques, and the implantable sensor device and external receiver have been explained in the context of intra-uterine monitoring, it will be understood that these techniques and structures could be applied to other body-cavity monitoring, such as within a vagina, bladder or digestive tract of a human or animal body.

The invention claimed is:

1. A monitoring system, comprising:
  a sensor device for generating sensor data, the sensor device having a secondary coil; and
  a receiver device having a controller, and a primary coil for wirelessly communicating with the sensor device, the receiver device being operable to wirelessly charge the sensor device via inductive coupling between the primary and secondary coils;
  wherein a quality factor of the primary coil is controllable;
  wherein the controller is operable to control the quality factor of the primary coil to be higher when the receiver device is wirelessly charging the sensor device than when the receiver device is receiving the sensor data from the sensor device;
  wherein the quality factor of the primary coil is selectable between a plurality of different levels;
  wherein the sensor device is an implantable sensor device;
  wherein the receiver device is operable to drive the primary coil at a frequency of order 100 kHz;
  wherein the sensor device is shaped and dimensioned for implantation in a uterus for measuring conditions within the uterus;
  wherein the receiver device is wearable;
  wherein the primary coil extends around a body of a user when the implantable sensor device is implanted in a substantially vertical orientation within the uterus of the user;
  wherein the primary coil is selectively configurable between a first mode in which it operates with a first quality factor and a second mode in which it operates with a second quality factor, and the second quality factor is lower than the first quality factor;
  wherein the controller is operable to select the second mode during a data transfer phase for receiving data from the sensor device and to select the first mode during a charging phase for charging the sensor device; and
  wherein the controller is operable during a further data transfer phase separate from the charging phase for wirelessly transmitting a signal to the sensor device, to select the second mode.

2. The monitoring system according to claim 1, wherein the quality factor is controllable by modifying an electrical resistance associated with the primary coil.

3. The monitoring system according to claim 1, wherein the receiver device comprises a coil circuit, the coil circuit comprising the primary coil and a damping resistor, the damping resistor being switched into series with the primary coil to reduce the quality factor of the primary coil.

4. The monitoring system according to claim 1, wherein the receiver device comprises a coil circuit, the coil circuit comprising the primary coil and a damping resistor, the damping resistor being switched into series with the primary coil to reduce the quality factor to configure the primary coil into the second mode.

5. The monitoring system according to claim 1, wherein the primary coil is a litz coil consisting of a plurality of insulated wires, and wherein the quality factor is controllable by selecting a number of the plurality of insulated wires through which an electric current passes during the wireless charging or the receiving of the sensor data.

6. The monitoring system according to claim 1, wherein the controller is operable to determine a data transfer performance, and to control the quality factor of the primary coil in dependence on the determined data transfer performance.

7. The monitoring system according to claim 6, wherein the controller is operable to determine the data transfer performance during a quality factor adjustment phase carried out prior to a transmission of the sensor data from the sensor device and/or prior to the transmission of a signal from the receiver device to the sensor device.

8. The monitoring system according to claim 1, wherein the primary coil comprises a plurality of turns, each turn extending around the body of the user, and each turn being formed of a litz wire.

9. The monitoring system according to claim 1, wherein the receiver device is one of a belt, a bra, an undergarment or a sanitary towel.

10. The monitoring system according to claim 3, wherein the sensor device is a biosensor for sensing one or more biophysical parameters of an environment around the sensor device.

11. A monitoring system comprising:
  a sensor device for generating sensor data, the sensor device having a secondary coil;
  a receiver device having a controller, and a primary coil for wirelessly communicating with the sensor device, the receiver device being operable to wirelessly charge the sensor device via inductive coupling between the primary and secondary coils;

wherein a quality factor of the primary coil is controllable;

wherein the controller is operable to control the quality factor of the primary coil to be higher when the receiver device is wirelessly charging the sensor device than when the receiver device is receiving sensor data from the sensor device;

wherein the sensor device is an implantable sensor device;

wherein the receiver device is operable to drive the primary coil at a frequency of order 100 kHz;

wherein the primary coil is selectively configurable between a first mode in which it operates with a first quality factor and a second mode in which it operates with a second quality factor, and the second quality factor is lower than the first quality factor;

wherein the sensor device is shaped and dimensioned for implantation in a uterus for measuring conditions within the uterus;

wherein the receiver device is wearable;

wherein the primary coil extends around a body of a user when the implantable sensor device is implanted in a substantially vertical orientation within the uterus of the user;

wherein the controller is operable to select the second mode during a data transfer phase for receiving data from the sensor device and to select the first mode during a charging phase for charging the sensor device; and wherein the primary coil is a litz coil consisting of a plurality of insulated wires, and wherein the quality factor is controllable by selecting a number of insulated wires through which an electric current passes during wireless charging or the receiving of sensor data, and wherein the primary coil is operated in the first mode by passing an electric current through a first proportion of the insulated wires, and is operated in the second mode by passing the electric current through a second proportion of the insulated wires, and a second number of the insulated wires in the second proportion of the insulated wires is lower than a first number of the insulated wires in the first proportion of the insulated wires.

12. The monitoring system according to claim 11, wherein the first proportion of the insulated wires is substantially all of the insulated wires within the litz coil.

13. The monitoring system according to claim 11, wherein the second proportion of the insulated wires is approximately 10% of the first proportion of the insulated wires.

14. A receiver device comprising a controller, and a primary coil for wirelessly receiving sensor data from an implantable sensor device having a secondary coil, the receiver device being operable to wirelessly charge the sensor device via electromagnetic inductive coupling between the primary and secondary coils;

wherein a quality factor of the primary coil is controllable;

wherein the controller is operable to control the quality factor of the primary coil to be higher when the receiver device is wirelessly charging the sensor device than when the receiver device is receiving the sensor data from the sensor device;

wherein the quality factor of the primary coil is selectable between a plurality of different levels;

wherein the receiver device is operable to drive the primary coil at a frequency of order 100 kHz;

wherein the sensor device is shaped and dimensioned for implantation in a uterus for measuring conditions within the uterus;

wherein the receiver device is wearable; and wherein the primary coil extends around a body of a user when the implantable sensor device is implanted in a substantially vertical orientation within the uterus of the user;

wherein the primary coil is selectively configurable between a first mode in which it operates with a first quality factor and a second mode in which it operates with a second quality factor, and the second quality factor is lower than the first quality factor;

wherein the controller is operable to select the second mode during a data transfer phase for receiving data from the sensor device and to select the first mode during a charging phase for charging the sensor device; and wherein the controller is operable during a further data transfer phase separate from the charging phase for wirelessly transmitting a signal to the sensor device, to select the second mode.

15. A method of using a receiver device to wirelessly charge an implantable sensor device using an inductive coupling between a primary coil of the receiver device and a secondary coil of the sensor device, and of wirelessly receiving sensor d ata from the sensor device at the receiver device via the primary and secondary coils, wherein the sensor device is implanted in a substantially vertical orientation within a uterus of a user for measuring conditions within the uterus, wherein the receiver device is wearable, and wherein the primary coil extends around a body of the user, wherein a quality factor of the primary coil is selectable between a plurality of different levels, the method comprising:

controlling a quality factor of the primary coil to be higher when the receiver device is wirelessly charging the sensor device than when the receiver device is receiving the sensor data from the sensor device, wherein the receiver device is operable to drive the primary coil at a frequency of order 100 kHz;

wherein the primary coil is selectively configurable between a first mode in which it operates with a first quality factor and a second mode in which it operates with a second quality factor, and the second quality factor is lower than the first quality factor;

wherein the controller is operable to select the second mode during a data transfer phase for receiving data from the sensor device and to select the first mode during a charging phase for charging the sensor device; and wherein the controller is operable during a further data transfer phase separate from the charging phase for wirelessly transmitting a signal to the sensor device, to select the second mode.

* * * * *